(12) United States Patent
Jaworski et al.

(10) Patent No.: US 6,773,679 B2
(45) Date of Patent: Aug. 10, 2004

(54) ELECTRIC FUMIGATION DEVICE

(75) Inventors: Thomas Jaworski, Racine, WI (US); Franco Zobele, Trento (IT); Paolo Campedelli, Mori-TN (IT); Walter Sordo, Trento (IT)

(73) Assignee: S. C. Johnson & Son, Inc., Racine, WI (US)

( * ) Notice: Subject to any disclaimer, the term of this patent is extended or adjusted under 35 U.S.C. 154(b) by 440 days.

(21) Appl. No.: 09/968,384

(22) Filed: Oct. 1, 2001

(65) Prior Publication Data

US 2003/0064002 A1 Apr. 3, 2003

(51) Int. Cl.[7] .............................. A61L 9/00; B01J 19/00; A62B 7/08; A61M 16/00; A01M 13/00
(52) U.S. Cl. ........................... 422/123; 422/1; 422/5; 422/28; 422/40; 422/120; 422/292; 422/305; 392/392; 43/125; 43/129; 219/275
(58) Field of Search ............................ 422/1, 5, 28, 40, 422/120, 123, 125, 292, 300, 305–307

(56) References Cited

U.S. PATENT DOCUMENTS

| | | | |
|---|---|---|---|
| 2,513,919 A | 7/1950 | Costello | 219/19 |
| 2,813,187 A | 11/1957 | Rovira | 219/19 |
| 3,872,280 A | 3/1975 | Van Dalen | 219/271 |
| 4,163,038 A | 7/1979 | Nishimura et al. | 422/36 |
| 4,171,340 A | 10/1979 | Nishimura et al. | 422/36 |
| 4,425,302 A | 1/1984 | Pons Pons | 422/125 |
| 4,687,904 A | 8/1987 | Melanson et al. | 219/271 |
| 4,703,155 A | 10/1987 | Suhajda | 219/271 |
| 4,731,522 A * | 3/1988 | Manchester | 392/390 |
| 4,777,345 A | 10/1988 | Manchester | 219/271 |
| 4,780,286 A | 10/1988 | Parent et al. | 422/125 |
| 5,095,645 A | 3/1992 | Borawski | 43/57.1 |
| 5,402,517 A | 3/1995 | Gillett et al. | 392/386 |
| 5,796,914 A | 8/1998 | Gatzemeyer et al. | 392/390 |
| 6,151,827 A * | 11/2000 | Smith et al. | 43/129 |
| 6,349,168 B1 * | 2/2002 | Jaworski | 392/392 |

* cited by examiner

Primary Examiner—Robert J. Warden, Sr.
Assistant Examiner—Monzer R. Chorbaji

(57) ABSTRACT

An electrically activatable fumigating device, methods of using it, and methods of constructing the device, are disclosed. The device is adapted to be plugged into a wall outlet. It is provided with a resistance heater that is housed in a lower recess of a heating cup by crimping edges of the recess around the heater. The cup focuses the heat of the heater adjacent the bottom of the cup. A eutectic thermal cut-off operates as a primary means of energy cut-off. The resistance heater is also designed to fail after a specified heating period as a redundant means of cut-off.

16 Claims, 3 Drawing Sheets

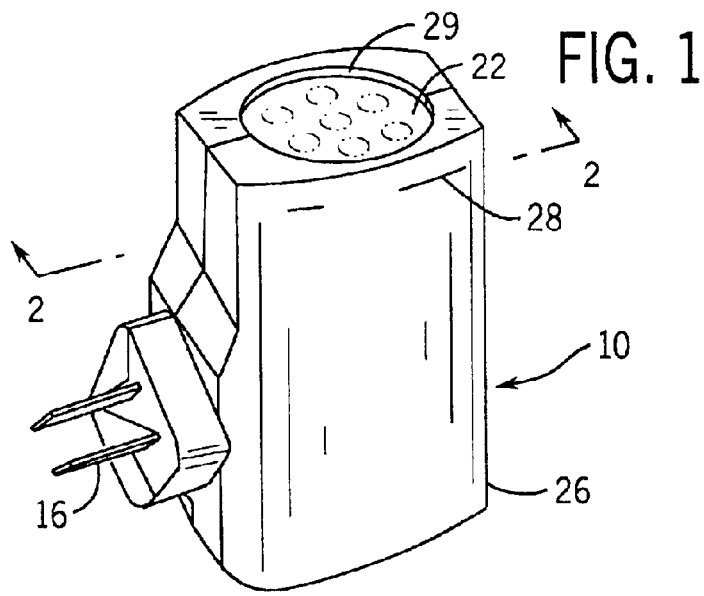
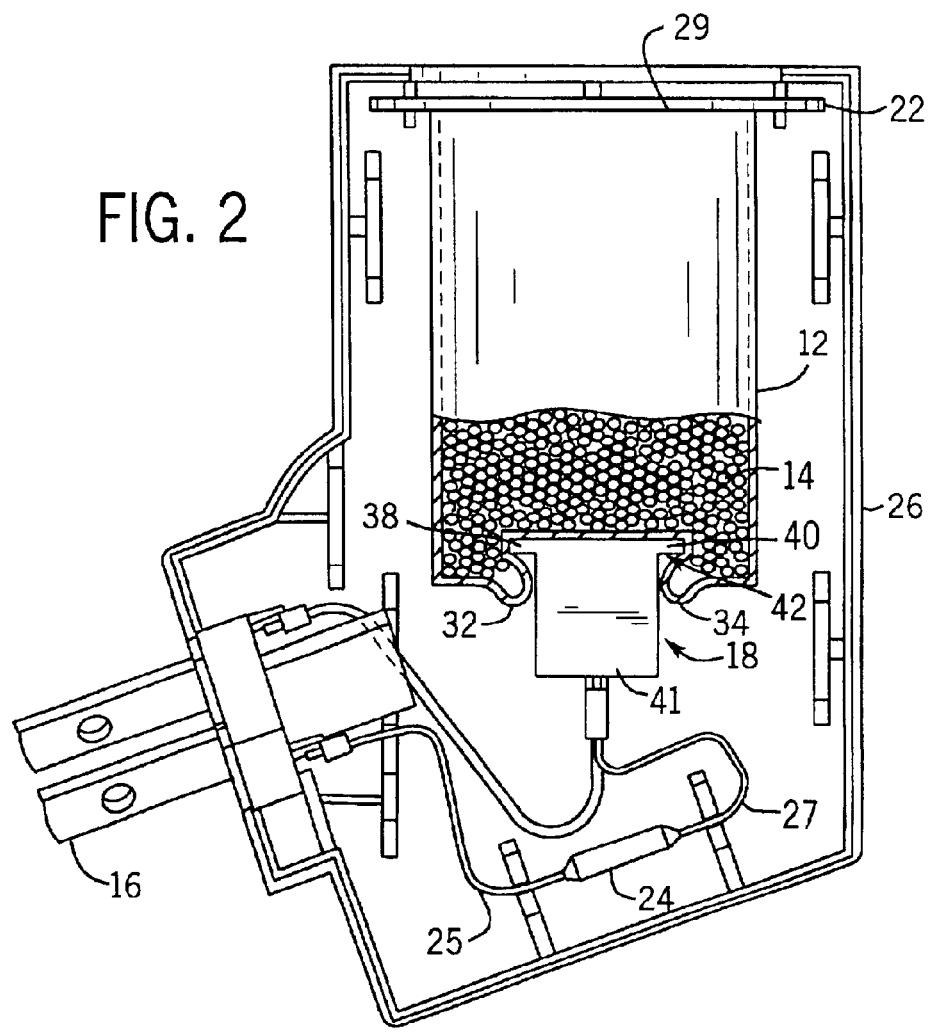

ELECTRIC FUMIGATION DEVICE

CROSS-REFERENCE TO RELATED APPLICATIONS

Not applicable

STATEMENT REGARDING FEDERALLY SPONSORED RESEARCH/DEVELOPMENT

Not applicable

BACKGROUND OF THE INVENTION

The present invention relates to wall mountable electrically activated fumigation devices. It provides devices with improved electrical efficiency and shut-off protection.

Devices are known for fumigating an enclosed area, such as a room in a house, by expelling a fumigant (e.g. typically an insecticide or fragrance) upon an application of heat. As disclosed in U.S. Pat. No. 5,796,914, some of these devices include a disposable canister containing the fumigant, and an electric heater positioned under the fumigant. When activated the device produces a fog that is expelled out to fumigate a room or the like.

Before the application of heat, the fumigant typically is in a solid form. It subsequently transforms into a viscous gel material in response to the initial introduction of heat. Further heating will produce the fog.

U.S. Pat. No. 3,872,280 is an example of an electrically heated vaporizer that also directly plugs into an electrical receptacle. U.S. Pat. Nos. 4,687,904, 4,777,345, and 4,780,286 all provide examples of electrically activated fumigation devices that utilize electricity to set off a charge of insecticide to fumigate a room. These latter devices then automatically disable or otherwise shut off as will be described below.

For example, the U.S. Pat. No. 4,687,904 device uses a positive temperature co-efficient ceramic heater ("PTC heater") to initiate the fogging. As the insecticide is volatilized, a lead-in wire is fused, interrupting the electrical circuit necessary to power the PTC heater. The fusible lead-in wire is incorporated within the structure of the canister so that the outside portion of the device may be reused by inserting a new canister with its new charge of insecticide and also with its new fusible lead-in wire.

The U.S. Pat. No. 4,777,345 device similarly utilizes the fusing of an electrical lead contained within a replaceable canister as a means of disabling or turning off a fumigating device. However, the wire that is fusible within the canister is itself a resistance heater wire, not a separate PTC heater.

The U.S. Pat. No. 4,780,286 device depends upon a PTC heater to activate a charge within a disposable canister. However, the heat of the reaction does not fuse a fusible lead-in wire. Instead it melts a eutectic metal connector, the loss of which again interrupts the electrical circuit to the PTC heater. Other devices of interest are described in U.S. Pat. Nos. 5,402,517, 5,095,647, 4,425,302, and 2,513,919.

While the above devices, and particularly U.S. Pat. No. 5,796,914, have been effective in controlling insects within confined spaces (or otherwise dispersing other desired volatiles such as fragrances and disinfectants), there is a continuing desire to focus the heat generated by the heating element at a particular location adjacent the material being heated, without significant heating of the outer casing. Further, it is desired to provide redundancy in the manner of shutting off the fumigator once it has started (to reduce incidence of overheating), and to provide protection against spilling if the device is mounted upside down in the wall socket.

BRIEF SUMMARY OF THE INVENTION

In one aspect the invention provides an electric fumigation device having an outer housing, an electrical plug extending from the outer housing, and a well mounted in the outer housing. The well has a well mouth that can open to the atmosphere and an outwardly open recess in a lower portion of a wall of the well, the well containing a heat-activatable fumigant. There is also a heater at least partially enclosed in the recess for heating the heat-activatable fumigant in response to electricity delivered via the electrical plug.

In preferred forms there is a eutectic thermal cut-off device ("TCO") that activates to automatically disable the heater at a predetermined temperature, and the outwardly open recess is downwardly open. In addition, the heater can itself create an open circuit when the heater reaches a predetermined temperature (if the TCO hasn't worked before then).

If the fumigating device is plugged in upside down the TCO will cause the dispenser to self-disable before the active ingredient is dispensed from the well. This is because the steel well will largely retain the heat of the heater near the recess long enough to trigger the cutoff, rather than immediately transferring the heat along the well to the fumigant which in an upside down positioning would be remote from the heater (such as aluminum might do).

The edges of the recess can be crimped around the heater to assist in retaining the heater in the recess, and walls of the well can be made of tin-coated steel having a thickness of between 0.25 and 0.5 millimeter (a preferred thickness is 0.35 mm). The heater that is placed in the recess can be a resistance heater designed to open (and thus cease to work) after heating to a selected temperature. For example, it can be a resistive film heater housed in a ceramic block.

The fumigant is preferably an insect control agent (e.g. insecticide, insect repellent, or insect growth regulator), a fragrance, and/or a disinfectant. The most preferred fumigant is permethrin. However, a wide variety of synthetic and naturally occurring insecticides would also work.

In another aspect the invention provides a method of fumigating an area having an electrical receptacle mounted on a wall with a fumigant. One provides a device of the above kind, plugs the device into the electrical receptacle, and allows electricity from the electrical receptacle to cause a release of the fumigant. There can also be a further step of disabling the heater when an area between the well and outer housing exceeds a thermal cutoff temperature. In an especially preferred method the device that is used also has a redundant second thermal cutoff.

In yet another form the invention provides a method for constructing such a fumigation device. One obtains a well having an open mouth at a first distal end and a downwardly extending recess in a second distal end. The downwardly extending recess has opposed first and second edges. One inserts a heater element including an upper flange into the downwardly extending recess, bends the opposed edges of the downwardly extending recess under the flange of the heater element, and places a fumigant in the well. One the encloses the mouth of the well with a cover, and electrically couples the heater element to an electrical plug.

The well contains a heat-activatable chemical charge, preferably in the form of pellets containing both an active ingredient and blowing agent for expelling the active ingredient from the well by a self-sustaining chemical reaction. The blowing agent may combust, or be a heat-activatable but non-combusting blowing agent such as azodicarbonamide.

The well mouth can be closed by a cover made of a material sufficiently impervious to water and atmospheric gases so as to be able to protect the chemical charge during storage, but openable by the blowing agent means to release fumigant at the well mouth. To accomplish this function, the cover may be capable of bursting, melting, or otherwise releasing fumigant in response to the temperature or pressure generated by the blowing agent means.

The heater is preferably a resistance heater designed to break or otherwise become discontinuous after heating to a select temperature, thereby interrupting the flow of the electricity through the fumigating device. Various resistance heaters are known to those skilled in the art, including heaters utilizing a loop or a wound coil of resistance wire. Another alternative heating means is a positive temperature co-efficient heater, commonly called a "PTC" heater. A positive temperature co-efficient heater may be made self-disabling by selecting its capacity to be such that it burns out and provides an open circuit when a desired temperature is reached.

The most preferred heater is a ceramic encapsulated metal film resistor heater. However, other resistance heaters also are within the breadth and scope of the invention, including wire wound resistors, foil heaters, resistive conductive patterns printed, etched, or otherwise formed on a supporting substrate, and the like.

In addition to employing heaters that break or self-consume, it is possible to provide a TCO selected to interrupt the flow of electricity through the fumigating device when the TCO is heated above a selected maximum temperature. This TCO can be of the "eutectic" type so as to disable the heater when temperatures within the fumigating device have risen above a selected maximum temperature.

The invention thus provides an electric fumigator that efficiently uses heat (as the heater directly transfers heat to the well through both its top and sides, reduces the risk of heating the fumigant when the device is plugged in upside down in a possible spill position (as the selection of materials and heater placement activates the safety shutoff—in this case the TCO—before fumigation would begin), minimizes the likelihood of the outer housing becoming too warm (due to the redundant thermal cutoffs), and which is relatively easy to assemble. Moreover, careful selection of the heater and eutectic cutoff can permit the device to be used with a wide variety of voltages, while retaining consistent cutoff.

The foregoing and other advantages of the invention will appear from the following description. In the description, reference is made to the accompanying drawings which form a part thereof, and in which there is shown by way of illustration, and not limitation, a preferred embodiment of the invention. Such embodiment does not necessarily represent the full scope of the invention. Reference must therefore be made to the claims herein for interpreting the scope of the invention.

BRIEF DESCRIPTION OF THE DRAWINGS

FIG. 1 is a perspective view of an electrical fumigation device of the present invention;

FIG. 2 is a partial sectional view taken along line 2—2 of FIG. 1;

DETAILED DESCRIPTION OF THE PREFERRED EMBODIMENT

Figure 3:
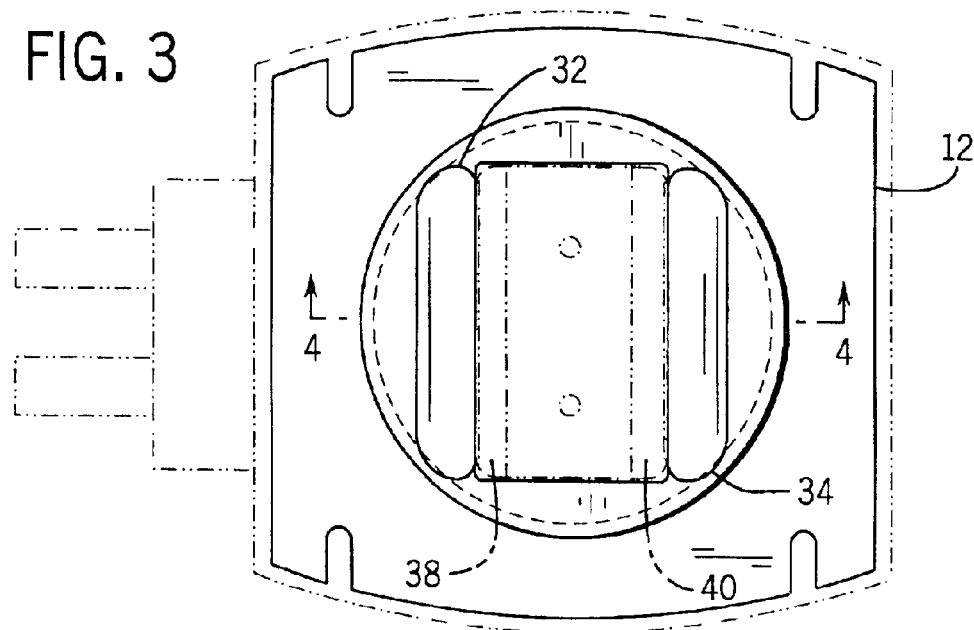
FIG. 3 is a top view of the well portion of FIG. 1, albeit without a top seal.

Referring now to FIGS. 1 and 2, an electrically activatable fumigation device 10 constructed in accordance with the present invention is shown. There is a well 12 containing a heat activatable chemical charge/fumigant 14, a heater 18, a eutectic type thermal cut-off device 24, and a plug 16. The chemical charge 14 is electrically heated by coupling the plug 16 to a standard electrical receptacle supplying a 120 VAC power supply, thereby providing electrical current to the heater. The well 12, heater 18, and eutectic thermal cut-off device 24 are enclosed in an outer housing 26. A vent opening 28 can be provided.

The heat-activatable chemical charge 14 preferably contains an active ingredient and blowing agent for expelling the active ingredient from the well by a self-sustaining chemical reaction. The blowing agent may combust or, preferably, be a heat-activatable but non-combusting blowing agent, such as azodicarbonamide. In a preferred embodiment, the heat-activated chemical charge 14 comprises an insecticide (permethrin), starch and a fragrance, where the chemical charge is in the shape of cylindrical pellets having a 5/32" diameter, which vary between 1/4 and 1/8" long.

Alternate blowing agents are also known to those of skill in the art. Furthermore, although pellets are the preferred form of the chemical charge, other forms of chemical agents including granulated and spherical can also be used.

At a first distal end the well 12 there is an open end or mouth 20 through which the heat activated chemical charge 14 can be released to the atmosphere. The mouth 20 is enclosed by a cover 22, preferably made of a material sufficiently impervious to water and atmospheric gases as to be able to protect the heat activated chemical charge 14 during storage, but openable by the blowing agent means to release fumigant at the well mouth 12. To accomplish this function, the cover may be capable of bursting, melting, or otherwise releasing fumigant in response to the temperature or pressure generated by the blowing agent means.

Figure 4:
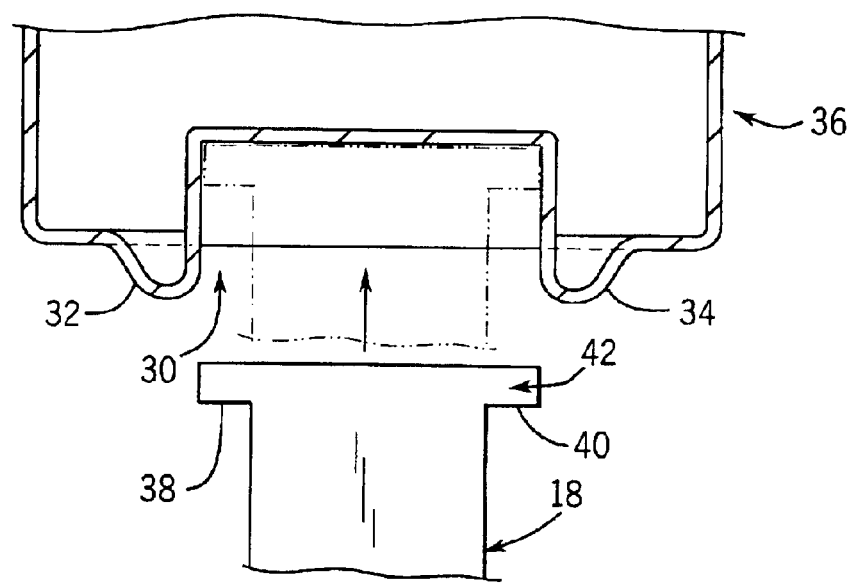
FIG. 4 is a partial exploded cross sectional view of the well of FIG. 3, taken generally along section line 4—4 of FIG. 3.

The well 12 further comprises a downwardly (or other outwardly directed) open recess 30 shaped and dimensioned to receive the heater 18. As best seen in FIG. 4, the edges of the recess 30 include first and second downwardly extending opposed edges 32 and 34 which extend vertically downward from opposing sides of the recess 30. The lips 32 and 34 are crimpable by compressive pressure from inside the well (compare FIG. 5) so as to provide a means for retaining the heater so that it is to a greater extent surrounded by the well. This directs the heat produced by the heater 18 specifically at the heat activated chemical agent 14 enclosed in the well 12.

The well 12 is constructed of a material having a lower thermal conductivity than the standard aluminum wells used with conventional foggers. Thus, to a greater extent, heat directed to the well 12 can be localized for a greater period of time adjacent the activatable chemical charge 14. For example, the well 12 can have walls made of tin plated steel which are 0.35 millimeter thick. Other suitable materials may be certain other metals, ceramics, certain temperature resistant plastics and glass.

Figure 6:
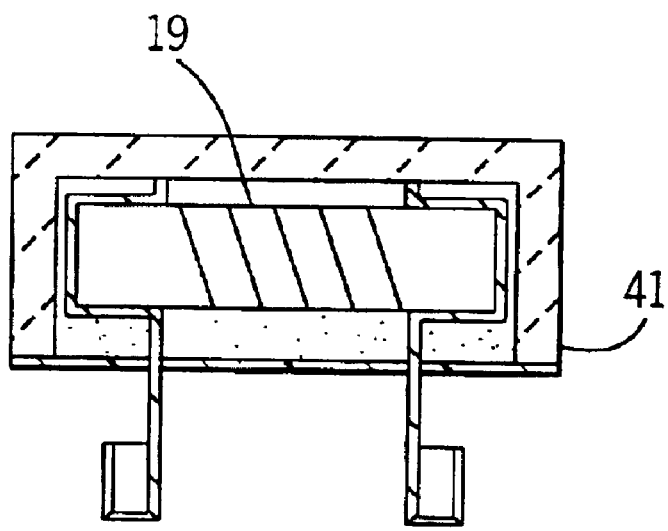
FIG. 6 is cross-sectional side view of the heater element portion of FIG. 2.

Referring still to FIG. 2 and also to FIG. 6, the heater 18 includes a resistor 19 encased on a ceramic block 41. The ceramic block 41 has a rectangular base section and an upper flange 42 sized and dimensioned to be tightly received in the downwardly open recess 30 of the well 12. The flange 42 includes two opposing edges 38 and 40 which extend horizontally beyond the base section and which are sized and dimensioned to be retained in place by the well edges 32 and 34.

The resistor 19 is preferably a metal film resistance heater selected to provide a temperature necessary to activate the heat-activated chemical agent 14, and to provide an open circuit when the temperature reaches a predetermined temperature level, thereby halting the heating process. Where the heat activated chemical agent comprises azodicarbonamide, the heater 18 can be selected to provide a minimum temperature of 250° C. at the inside bottom of the well 12, to maintain this minimum temperature for 30 seconds, and to self-terminate thereafter in the event that the eutectic thermal cut-off device 24 does not open as described below. A preferred resistor is manufactured by Royal Electric Fty., Co., Ltd., has a resistance value of 600 ohms plus or minus 5 percent, and operates over a range of expected input power line voltages of 120 volts plus or minus 10 percent.

The selected metal film resistor has been experimentally shown to open-circuit or self-disable at temperature and current levels similar to those which activate the thermal cutoff device ("TCO") 24. The metal film resistor, therefore, provides a comparatively quick back-up mechanism to the TCO 24. Additionally, because the heater 18 is mounted on the well 12 and crimped in place, the position of the heater 18 is stable, and is not likely to contact the plastic housing.

Although a metal film resistor encased in a rectangular ceramic block has been described in connection with the preferred embodiment of the heater 18, other non-renewable resistance heaters can also be used. Such resistance heaters can include wound wire coils, positive temperature coefficient heaters or PTC heaters which burn out or become discontinuous when a predetermined temperature is reached. Other suitable resistors will be apparent to those of ordinary skill in the art.

Referring still to FIG. 2, the heater 18 is electrically coupled in series between the plug 16 and the eutectic thermal cut-off device 24. The eutectic thermal cut-off device 24 is thermally activated to open at a predetermined temperature, thereby preventing the outer housing from becoming too hot. The eutectic thermal cut-off device 24 provides a primary thermal cut-off, with the heater 18 providing a secondary, backup, thermal cut-off in the event that the eutectic thermal cut-off device 24 does not open.

The eutectic cut-off device 24 is electrically coupled in series between the heater 18 and plug 16. The TCO 24 includes a first lead 25 which is coupled, attached to one blade of the plug 16, and a second lead 27 which is coupled to the heater 18. To provide a highly repeatable cut-off temperature, the length of the leads 25 and 27 are calculated to provide a known additional thermal resistance value to the TCO 24.

A suitable eutectic thermal cut-off device 24 is provided by Anzen Dengu Co., Ltd. The specified part is part number v169 having a rated functioning temperature of 169° C. The v169 eutectic thermal cut-off device including leads constructed of a tin or solder plated copper and having a diameter of 0.58 millimeters. The device is further rated to operate at a voltage of 250V and current of 2A.

To effectively open the circuit at the rated cut-off temperature of 169° C., the preferred length of lead 27 has been determined to be substantially thirty-one millimeters. Lead 27 provides an additional thermal resistive element to the eutectic thermal cut-off device, and also allow the eutectic thermal cut-off device 24 to be located a selected distance from the heater 18, thereby preventing the TCO 24 from opening prematurely due to heat produced by the heater 18. It will be apparent that the selected lead length is dependent on a number of different factors including the selected TCO device, lead material and construction, heater element, and the selected method of attaching the leads to other components of the system. For example, although other suitable eutectic thermal cut-off devices 24 are available, such as those produced by the Uchihashi Estec Co., Ltd. and Joint Force Metal Research Co., to provide an accurate cut-off temperature, the lead length should be recalculated for use with these TCO devices.

Furthermore, differences in construction, such as the use of soldering or other joining techniques instead of crimping, or the use of other materials in the blade can affect the activation temperature. Therefore, adjustments to the lead length may be required when using alternative materials.

Figure 5:
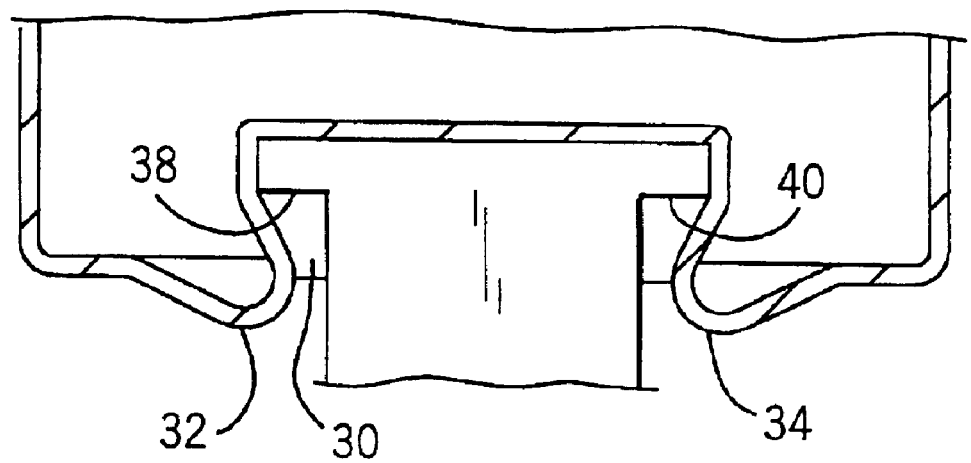
FIG. 5 is a view similar to FIG. 4, albeit after insertion of the heater device and bending of the edges of the recess around it.

Referring now to FIGS. 3–5, the assembly of the heater 18 in the downwardly extending recess 30 of the well 12 is shown. The heater 18 is initially inserted into the downwardly open recess 30 such that the flange 42 rests against the bottom of the well 12. After the heater 18 is positioned in the downwardly open recess 30, a crimping tool (not shown) is inserted through the mouth 20 of the well 12. The crimping tool is applied to the edges 32 and 34 to form the edges 32 and 34 over the edges 38 and 40 of the flange 42, such that the edges 32 and 34 form a retention means for retaining the heater 18 in the downwardly extending recess, 30 as shown in FIG. 5.

Referring again to FIGS. 1 and 2, in operation the electrically activated fumigation device 10 is electrically coupled to a standard wall electrical receptacle by means of the plug 16. When the plug 16 is coupled to a common household voltage supply such as a 120 volt AC power supply, a current flows through the heater 18 and the eutectic thermal device 24. If the electrical fumigation device 10 is plugged into the receptacle correctly, such that the mouth 20 of the well 12 is directed upward and the heat activated chemical agent 14 rests in the bottom of the well 12, the heater 18 applies heat to the heat activated chemical agent 14, causing the blowing agent to activate, and distributing the fumigation chemicals through the cover 22. As noted above, the well 12 is constructed of a material having a low thermal conductivity which therefore concentrates the heat on the chemical agent 14, and minimizes the spread of heat to the outer housing 26 or elsewhere within the electrically activated fumigation device 10.

The insertion of the heater 18 into the downwardly extending recess 30 additionally serves to concentrate the heat generated by the heater 18 on the chemical agent 14, which is positioned in the well 12 both directly above the heater 18 and also adjacent the sides of the heater 18. The dispersion of the chemical agent 14 adjacent the side of the heater 18 aids in heating the chemical agent 14 evenly and quickly.

About the time that the chemical agent 14 has dissipated, the temperature of the resistor has increased such that the cutoff devices begin to activate. For example, the device 10 can be disabled when the eutectic thermal cut-off 14 reaches the cut-off temperature, or when the heater 18 reaches the predetermined temperature at which the resistive element of the heater 18 opens.

If the user inserts the electrically activated fumigation device 10 into an electrical receptacle incorrectly, such that the mouth 20 of the well 12 faces downward, little or no heat is dissipated though the chemical agent 14, and the temperature around the cutoffs rises well before the volatile is dispensed. Thus, the user will not accidently spill the gelled material onto the floor.

In employing the components of the preferred embodiment, as described above, at 120 VAC the current flow through the heater 18 is normally above two hundred milliamps. As current continues to flow through the device, the resistor 19 in the heater 18 begins to fail, initially allowing the current to increase or "ramp up" to a level ranging between 300 and 500 mA. As the resistor continues to heat, an open circuit eventually develops in the resistive film, causing the current flow through the device to drop to zero.

When operated at a voltage level of 120 VAC or more, the amount of time required for the heater 18 to open circuit has been shown generally to be greater than the time required for the TCO 24 to open. Under these operating conditions, the TCO 24 generally disables the electrical fumigation device 10. When the input line voltage to the plug 16 is low, for example 108 VAC, the operating current of the device is lower, generally starting at a value of less than 200 mA and increasing slightly thereafter. At this lower operating voltage, the current through the heater 18 sometimes ramps up, as described above with reference to the 120 VAC operating voltage, but can also provide an open circuit without ramping up.

When the heater 18 open circuits quickly without the current ramping, the heater 18 can disable the electrical fumigating device 10 rather than the TCO 24. In either case, if the TCO 24 fails to activate, the heater 18 provides a secondary failure mechanism to disable the electrical fumigation device 10 after the heat activated chemical agent is dispersed. Thus, the extra cutoff not only provides redundancy, it provides flexibility insofar as the supply voltage.

While a preferred embodiment has been shown, it should be appreciated that the device can be modified without departing from the spirit or scope of the claims. For example, although a eutectic thermal cut-off device has been shown and described, it will be apparent that other types of fuse devices could be employed in the invention. Furthermore, although a metal film resistor has been described as a component of the heater element, other types of resistors could also be used. Furthermore, although a plug suitable for use in a conventional North American electrical receptacle has been shown, other plugs and means for electrically coupling the fumigation device to a power supply could also be used.

Thus, the invention should not be limited to the specific materials or structures described above. The following claims should be looked to in order to understand the full scope of the invention.

Industrial Applicability

The invention provides a fumigating device with more efficient heat use and shut-down features.

We claim:

1. An electrically activatable fumigating device, comprising:
   an outer housing;
   an electrical plug extending from the outer housing;
   a well mounted in the outer housing, the well having a well mouth that can open to the atmosphere and an outwardly open recess in a lower portion of a wall of the well, the well containing a heat-activatable fumigant; and
   a heater at least partially enclosed in the recess for heating the heat-activatable fumigant in response to electricity delivered via the electrical plug.

2. The fumigation device as recited in claim 1, further comprising a eutectic thermal cut-off device that activates to automatically disable the heater at a predetermined temperature.

3. The fumigation device as recited in claim 1, the outwardly open recess is downwardly open.

4. The fumigation device as recited in claim 1, wherein the heater provides an open circuit when the heater reaches a predetermined temperature.

5. The fumigation device as recited in claim 1, wherein the edges of the recess are crimped around the heater to assist in retaining the heater in the recess.

6. The fumigation device as recited in claim 1, wherein the well is made of steel.

7. The fumigation device as recited in claim 1, wherein walls of the well are made of tin-coated steel having a thickness of between 0.25 and 0.5 millimeter.

8. The fumigation device as recited in claim 1, wherein if the fumigating device is plugged in upside down the device will self-disable before the active ingredient is dispensed from the well.

9. The fumigation device as recited in claim 1, wherein the heater is in the form of a resistance heater designed to open after heating to a selected temperature.

10. The fumigation device as recited in claim 1, wherein the resistance heater is a resistive film heater housed in a ceramic block.

11. The fumigation device as recited in claim 1, wherein the fumigant is selected from the group consisting of insect control agents, fragrances, and disinfectants.

12. A method of fumigating an area having an electrical receptacle mounted on a wall with a fumigant, the method comprising the steps of:
    providing a device of claim 2;
    plugging the fumigating device into the electrical receptacle; and
    allowing electricity from the electrical receptacle to cause a release of the fumigant.

13. The method of claim 12, comprising the further step of disabling the heater when an area between the well and outer housing exceeds a thermal cutoff temperature.

14. The method of claim 12, wherein the device further comprises a redundant second thermal cutoff device.

15. A method of constructing the fumigation device of claim 1, comprising the steps of:
    obtaining a well comprising an open mouth at a first distal end and a downwardly extending recess at a second distal end, the downwardly extending recess comprising opposed first and second edges;
    inserting a heater element including an upper flange into the downwardly extending recess;
    bending the opposed edges of the downwardly extending recess under the flange of the heater element;
    placing a fumigant in the well;
    enclosing the mouth of the well with a cover; and
    electrically coupling the heater element to an electrical plug.

16. The method of claim 15, comprising the further step of electrically coupling a thermal cutoff device in series with the heater element.

* * * * *